United States Patent [19]

Reuschel

[11] Patent Number: 5,097,837
[45] Date of Patent: Mar. 24, 1992

[54] SYNCHRONOUS DEMODULATOR

[75] Inventor: Joerg Reuschel, Sindelfingen, Fed. Rep. of Germany

[73] Assignee: Hewlett-Packard Company, Palo Alto, Calif.

[21] Appl. No.: 398,230

[22] Filed: Aug. 24, 1989

[30] Foreign Application Priority Data

Sep. 17, 1988 [EP] European Pat. Off. ........ 88115271.4

[51] Int. Cl.⁵ .............................................. A61B 8/02
[52] U.S. Cl. ............................................. 128/661.07
[58] Field of Search .............. 128/661.07–661.10, 128/662.03–667.04; 73/861.25; 329/313, 314, 318, 323, 336, 346

[56] References Cited

U.S. PATENT DOCUMENTS 3,813,654  5/1974  Clifton et al. ............... 128/661.07
3,898,653  8/1975  Ban et al. ..................... 343/7 ED
4,010,424  3/1977  Faulkner ........................ 340/9
4,848,355  7/1989  Nahamura et al. .......... 128/661.07

FOREIGN PATENT DOCUMENTS 0204192  8/1989  European Pat. Off. .
2160731A  12/1985  United Kingdom .

OTHER PUBLICATIONS

Kardiotokograph zur uberwachung Der Fetal-Herafrequenz, 2087, Elektronik, vol. 26, No. 7, 1977, Juillet.
"Analog-Digital-Conversion Handbook", edited by David H. Sheingold, Prentice-Hall, Englewood Cliffs, N.J. 07632, (1986), pp. 565–568.

Primary Examiner—Francis Jaworski
Attorney, Agent, or Firm—Woodcock, Washburn, Kurtz, Mackiewicz & Norris

[57] ABSTRACT

A synchronous demodulator for the demodulation of ultrasound burst waves reflected by a moving object comprises an operational amplifier forming an integrator. When a MOSFET switch in the input line of the amplifier is conductive, it operates as a low-pass filter. If, on the other hand, this switch is in the high-impedance state, the actual value is stored by the capacitor. The circuit is switched between filtering mode and hold mode by a demodulator clock. The circuit incorporates the functions of demodulator, a low-pass and a hold circuit.

10 Claims, 5 Drawing Sheets

SYNCHRONOUS DEMODULATOR

BACKGROUND OF THE INVENTION

This invention relates to a synchronous demodulator for the demodulation of ultrasound burst waves reflected by a moving object, such as, for example, in a cardiotocograph to determine the fetal heart rate.

Fetal monitoring, i.e. monitoring of the fetal condition during gestation and at birth, usually comprises monitoring of the uterus activity (toco) and of the fetal beat-to-beat heart rate (FHR). Among these, the fetal heart rate is the more important parameter as it gives an indication whether the fetus is sufficiently supplied with oxygen. Of course, both parameters may also be used for further diagnostic statements. In particular, the relation between fetal heart rate and labor allows one to evaluate the fetal condition.

To obtain a signal indicative of the fetal heart rate, a so-called fetal scalp electrode ma be applied to the fetal skin. These electrodes are usually spiral electrodes which are screwed the fetal epidermis (see for example U.S. Pat. No. 3,827,428). The electrodes allow very accurate measurements due to the excellent signal quality. Unfortunately, this so-called internal or direct measurement can only be used after rupture of the membranes. Prior to that point in time (in particular, during gestation), indirect methods must be used. These indirect measurements are performed abdominally, e.g., by listening to the fetal heart sound or by measuring the Doppler shift of an ultrasound wave reflected by the moving fetal heart.

The ultrasound technique is the most common one. According to this technique, an ultrasound transducer is placed externally on the pregnant woman's abdomen. The ultrasound signal is received by piezoelectric crystals. The Doppler shift of the reflected ultrasound wave is directly related to the speed of the moving parts (in particular, the walls) of the fetal heart.

Advanced technologies do not use continuous ultrasound waves for the described purpose, but bursts of ultrasound waves instead. The major advantage of the burst technique is, due to the fact that the reflected burst is delayed with respect to the transmitted burst, that a single piezoelectric crystal may be used both as a transmitter and as a receiver. Of course, it is also possible to use a multiplicity of crystals, each of these crystals acting as a transmitter as well as a receiver. A further advantage of the burst technique is that signals reflected in a certain depth of the body may be selected by adjusting a reception period or interval, i.e., by a "time window". By means of this "depth selection", the monitor is able to distinguish between signals resulting from the movements of the fetal heart and other signals, see for example EP-A-204 192.

The received ultrasound wave has to be demodulated in order to obtain the Doppler frequency not as a frequency shift of the high-frequency signal, but rather as a low frequency signal. It is already known to obtain this demodulation by mixing the received ultrasound signal with a square wave high-frequency (which corresponds to the transmitter frequency) signal. According to this method, the received ultrasound wave is switched on and off with the rate of this square-wave signal By this operation, a Doppler signal in the low-frequency range is generated. Still the generated signal contains a lot of other frequency components. Therefore, the signal obtained by mixing the received ultrasound wave with that square-wave signal has to pass a highly selective filter. A major disadvantage of this technique is that the received signal is extremely attenuated thus decreasing the precision of FHR determination. For example, the attenuation caused by the fact that the received signal is switched off for 50% of the available time results in an attenuation of $-6$ dB. A further, considerably larger attenuation is effected by the interval between two bursts. For example, if we assume a burst length of 5 $\mu$s and a repetition rate of the bursts of 3.2 kHz (which corresponds to a repetition interval of 312.5 $\mu$s), this results in an attenuation of $-36$ dB. The overall attenuation is therefore $-42$ dB. This attenuation is considerable and impairs the quality of the Doppler signal and, therefore, the detected fetal heart rate. This considerable attenuation cannot simply be compensated by an amplifier as such an amplifier generates additional noise.

In advanced technologies, the duration of the burst is adjustable, whereas the burst repetition rate remains constant. In such an application, the known demodulator circuit has the additional disadvantage that the attenuation is not constant when the burst length is varied. This implies additional inaccuracies of the obtained result.

SUMMARY OF THE INVENTION

In accordance with this invention, a preferred embodiment of the invention comprises a synchronous demodulator for the demodulation of ultrasound burst waves reflected by a moving object comprising ultrasound transmitting means emitting bursts of high frequency ultrasound waves, ultrasound receiving means for receiving the ultrasound waves which are reflected by the moving object wherein the ultrasound receiving means includes a demodulator circuit which isolates a signal indicative of the Doppler component of the reflected ultrasound signal in order to determine the speed of the moving object in relation to the ultrasound transmitting means.

In accordance with one important aspect of the invention, the demodulator circuit comprises an integrating circuit having a time constant which is considerably longer than the duration of a single oscillation of the high frequency, an actuatable switch coupled to the input of the integrating circuit, means for actuating the actuatable switch to a closed position with the high frequency at least during reception periods and means for holding the output value of the integrating circuit during the time intervals when the first actuatable switch is open.

The integrating circuit, therefore, has two basic operating modes. These are a low-pass filter mode and a hold mode. Switching between these modes is performed by the actuatable switch in the input line of the integrating circuit. This switch is actuated with the high frequency of the ultrasound waves, preferably 1 MegaHertz (MHz). During the time intervals when the switch is closed, i.e., the integrating circuit is connected with the received signal, it acts as a low-pass filter therefore performing the demodulation of the signal. During the periods where this switch is open, it acts as a hold circuit thereby avoiding the significant attenuation of the prior art circuit. This is particularly true as the signal is also held in the time intervals between two bursts. Actuation of this switch may be restricted to certain "reception periods" where a signal from the fetal heart is expected.

For the purpose of this application, the integrating circuit will be referred to as "low-pass filter" when the actuatable switch is closed. Still it is evident to anybody skilled in the art that a low-pass filter also fulfills the function of an integrator. Further, the integrating circuit will be referred to as "hold circuit" or "storage circuit" when the switch is open. The circuit holds its actual value in this case. It is evident to those skilled in the art that an integrator receiving a "0" signal at its input holds its last value.

The present invention, therefore, provides a synchronous demodulator which basically combines three functions:

1. It demodulates the received signal, i.e. operates as a demodulator,
2. it performs a low-pass filter function to suppress high frequency components and
3. it operates as a hold circuit.

The major advantages of the new demodulator are that significant attenuation can be avoided, that constant attenuation is guaranteed (which is particularly important if the burst length is varied), that the noise is shifted to very low frequencies which are not in the frequency band of the Doppler signal and that—in contrast to prior art solutions—only a few components are required.

Preferably, the integrating circuit according to the invention comprises an operational amplifier. This ensures high input impedance. Further, an operational amplifier may very easily be wired as an integrating circuit. Advantageously, a feed back capacitor is used for this purpose which may also act—in a second mode of operation—as a storage element. As soon as the actuatable switch is opened, the feed back capacitor is isolated from any current-draining elements and therefore keeps its charge up to the next cycle.

In a preferred embodiment, a second actuatable switch is arranged between the input of the first actuatable switch and a reference potential, the second actuatable switch being actuated in phase opposition to the first actuatable switch. In this case, the demodulator circuit operates in a "push-pull" chopping mode. Major advantages of this embodiment are:

1. The input is charged with a constant load (this is particularly true if several paths are connected to the input line—in this case, eventual crosstalk may be avoided),
2. no tight coupling over the first actuatable switch (which has a parasitic capacity) can occur, and
3. the first actuatable switch cannot change its state without being actuated (which may occur when this switch is of the field effect transistor type).

In general, FETs (field effect transistors) are preferred as switches in the present invention. In particular, these transistors ensure that the storage element (like a capacitor) is subject to good isolation in the hold mode.

It is understood that the present invention is not limited to monitoring of the fetal heart rate, but may also be useful in other ultrasound applications, e.g. for monitoring of fetal movement.

The invention also relates to a method for demodulating an ultrasound signal consisting of high-frequency burst waves being reflected by a moving object, preferably the fetal heart. According to this method, the ultrasound signal is fed to a circuit alternately operating as a low-pass filter or a storage (hold) circuit whereby the low-pass filter/storage circuit is switched between its two modes by an actuating signal of the high frequency. This ensures low attenuation with a low component count. Preferably the actuating signal is only applied to the low-pass filter/storage circuit at a certain distance. This helps to distinguish between objects at different distances from the transducer and to select one of these objects. In particular, it is possible to distinguish between ultrasound signals reflected by the fetal heart and signals reflected by other tissue, e.g. maternal muscles. In this embodiment, the low-pass filter/storage circuit operates as a storage circuit in the periods between said reception periods or "time windows".

Advantageously, the actuating signal actuates a switch in the input line of the low-pass filter storage circuit. Thereby, component count may be further reduced. In a preferred embodiment, the inverse of said actuating signal actuates a second switch connecting the input of the first switch with a reference potential, preferably 0 Volts, resulting in a "chopper" operation of the whole circuit.

Other features and advantages of the invention will become apparent from the following more detailed description, taken in conjunction with the accompanying drawings, which illustrate, by way of a non-limiting example, the principle of the invention.

DETAILED DESCRIPTION OF A PREFERRED EMBODIMENT

Figure 1:
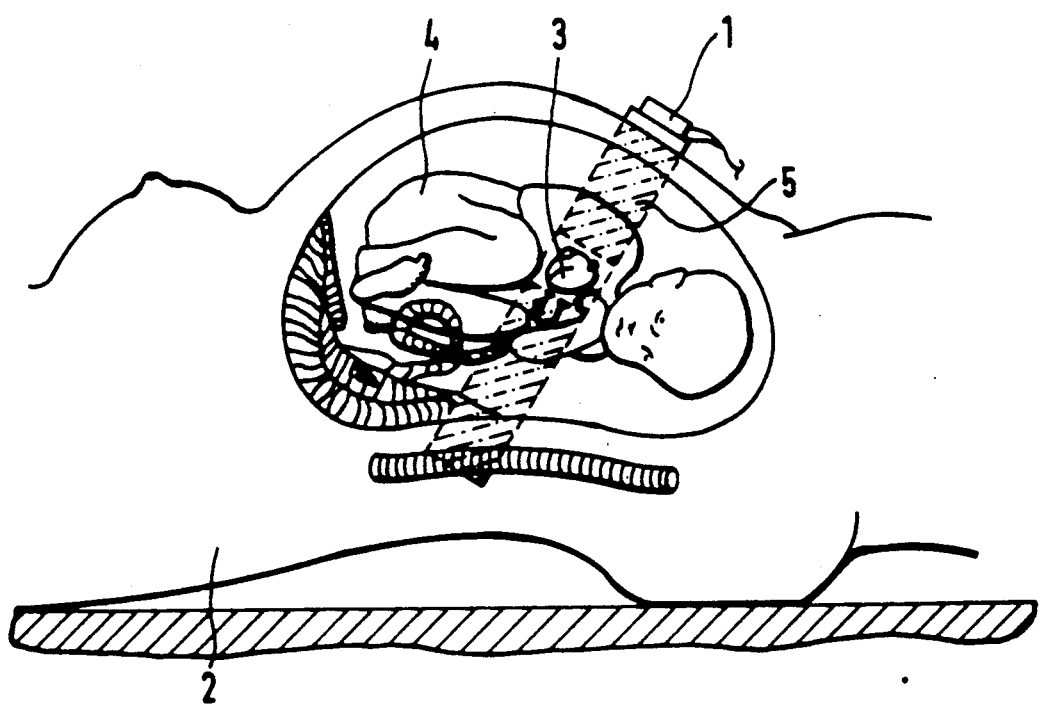
FIG. 1 depicts a typical application of an ultrasound transducer to monitor the fetal heart rate.

FIG. 1 depicts a typical application of an ultrasound transducer to monitor fetal heart rate. The ultrasound transducer 1 is applied to the abdomen of a pregnant woman 2. The ultrasound transducer 1 contains one or more piezoelectric crystals which are operated intermittently, i.e. with ultrasound burst waves. During a transmitting period, these crystals operate as transmitter crystals, whereas, during a reception period, they operate as receivers. Thereby, the same piezoelectric crystal is operated as a transmitter as well as a receiver.

An important diagnostic information during gestation and at birth is the fetal beat-to-beat heart rate, i.e. the heart rate calculated as the inverse of the time interval between two subsequent heart beats. This information may be obtained by the Doppler shift of the ultrasound waves reflected by the moving walls of the fetal heart 3. As the position of fetus 4 is not constant, ultrasound beam 5 must be either adjusted carefully to intersect with the fetal heart, or other techniques, like the appliance of a wide beam ultrasound signal and subsequent filtering, e.g. by auto correlation, must be used. The "burst" technique is used to distinguish between objects in various distances to the ultrasound transducer 1 as only the movements of the walls of the fetal heart are of interest and no maternal contractions or the like. This may be performed by using a receiving "time window" so that only signals reflected in a certain distance to the ultrasound transducer are further processed.

Although the present invention is primarily intended for use in such fetal monitoring applications, it is not restricted to this kind of application.

Figure 2:
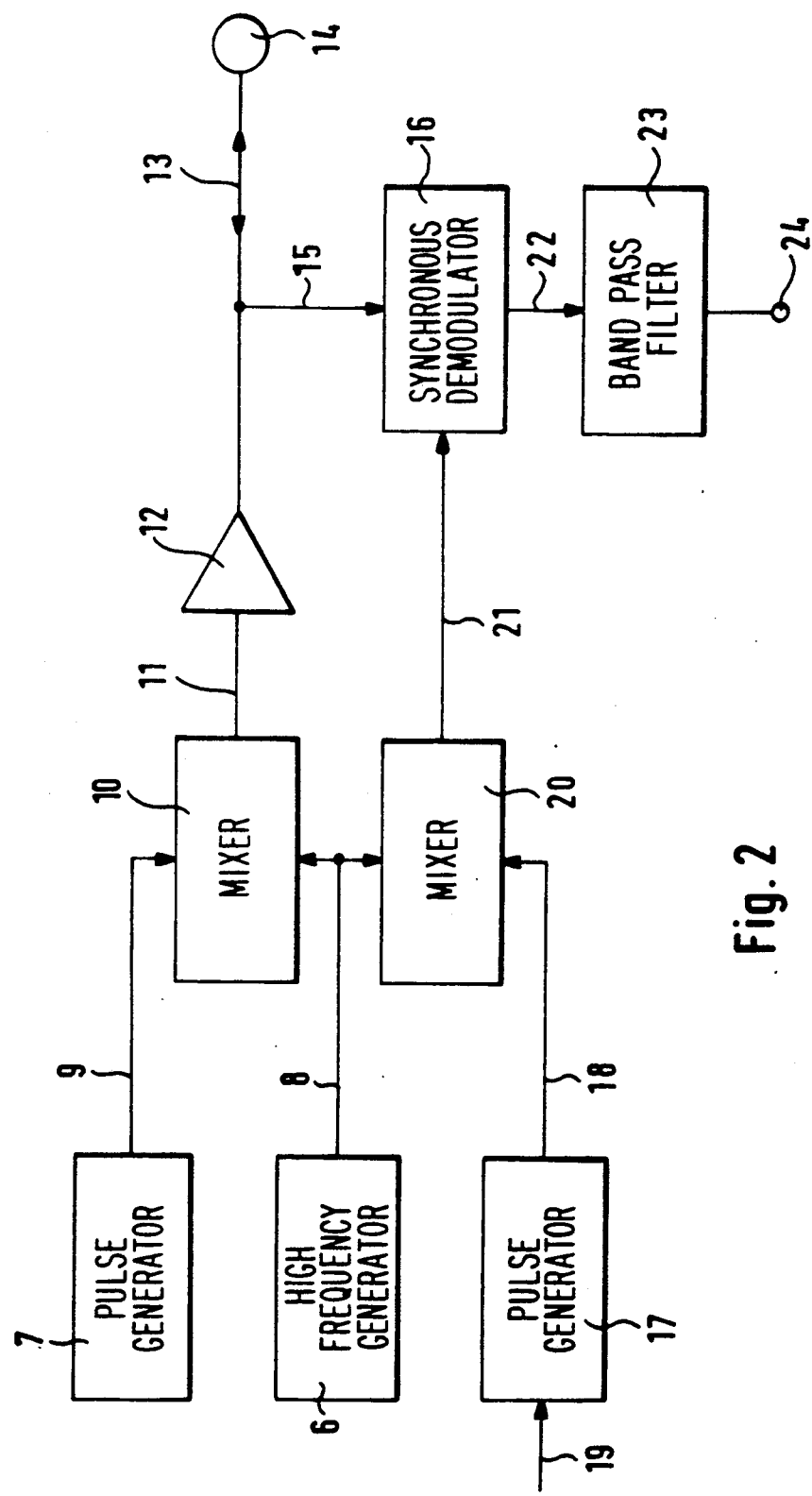
FIG. 2 is an overall block diagram of the transmitter/receiver section of the ultrasound channel.

FIG. 2 depicts an overall block diagram of the ultrasound transmitting/receiving section for an ultrasound transducer. According to FIG. 2, a 1 MegaHertz (MHz) high-frequency signal is generated by HF (high frequency) generator 6. A pulse generator 7 generates bursts of a length of 15 $\mu$s or longer at a repetition rate of 3.2 kHz (KiloHertz), i.e. a pulse is generated every 312.5 $\mu$s.

The signals generated by HF generator 6 and pulse generator 7 are fed (lines 8 and 9) to a mixer circuit 10. Mixer 10 performs an "AND" combination of the incoming signals and generates high-frequency bursts which are fed (via line 11) to an amplifier 12. The output of amplifier 12 is fed (via bidirectional line 13) to the ultrasound transducer which is referred to as 14 in this figure.

Figure 4:
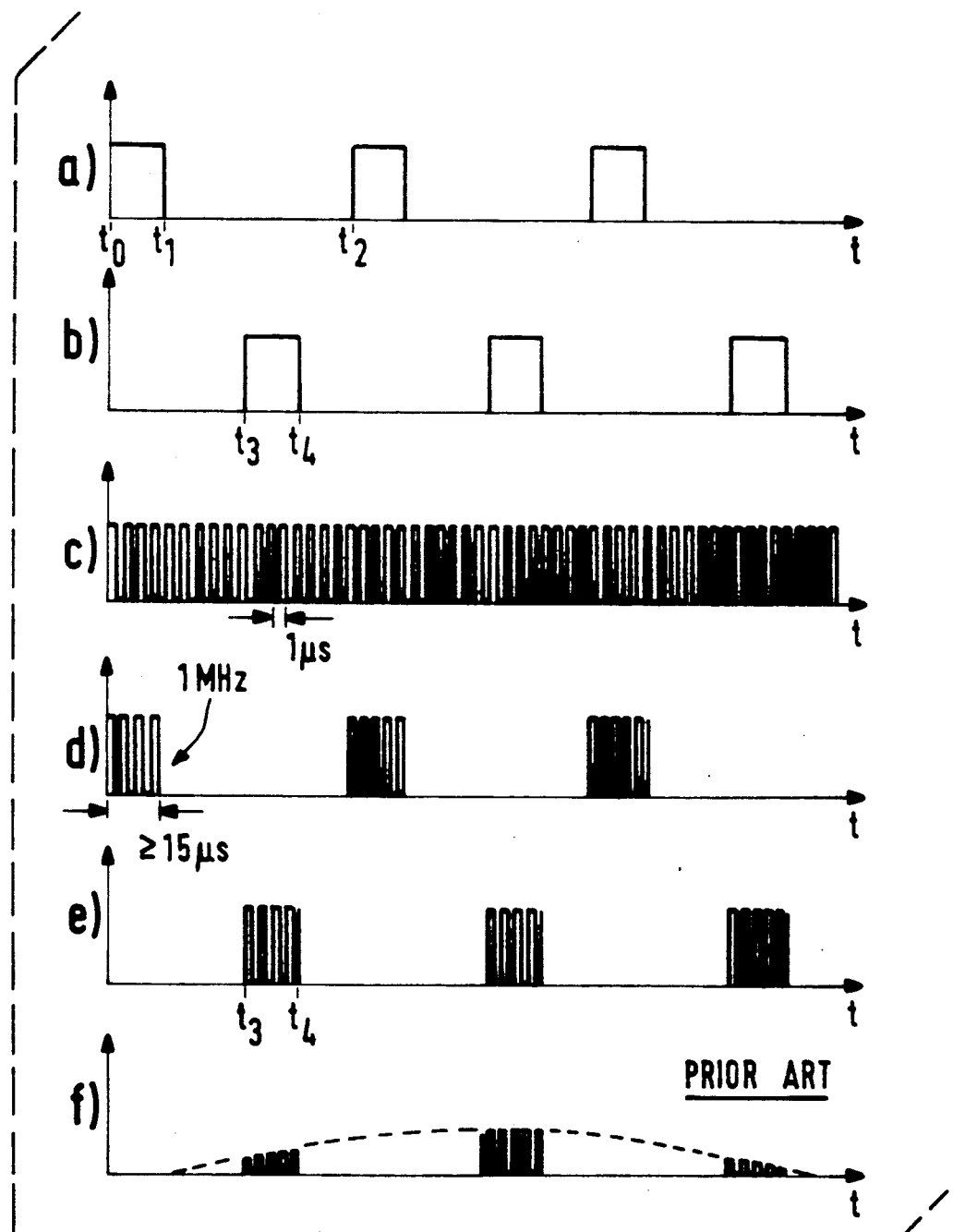
FIGS. 4a to 4f depict timing diagrams of certain signals occurring in the circuit of FIG. 2.

The timing diagram of this transmitting section is depicted in FIG. 4. FIG. 4c shows the 1 MHz high-frequency signal generated by HF generator 6. The pulses generated by pulse generator 7 are depicted in FIG. 4a; they have a pulse width of $t_1 - t_0 = 15$ $\mu$s and more and a repetition rate of 3.2 kHz, i.e. the delay between two subsequent pulses is $t_2 - t_0 = 312.5$ $\mu$s. The resulting signal generated by mixer 10 is depicted in FIG. 4d; this signal consists of single bursts with the duration of 15 $\mu$s and more, a repetition rate of 3.2 kHz and containing a HF signal of 1 MHz.

As already mentioned, ultrasound transducer 14 is also operated as a receiver. In this mode of operation, the received signal, i.e. the signal reflected by the moving walls of the fetal heart, is fed via bidirectional line 13 and line 15 to a synchronous demodulator 16. This synchronous demodulator is used to detect the Doppler shift of the received ultrasound signal as this Doppler shift is related to the speed of the moving walls of the fetal heart.

A second pulse generator 17 generates signals to establish a "time window" for the reception of the ultrasound signal. A timing diagram of the signal generated by this pulse generator (on line 18) is depicted in FIG. 4b. The pulses shown there are delayed with respect to the pulses generated by pulse generator 7 (FIG. 4a), i.e. $t_3 > t_0$. The pulses generated by pulse generators 7 and 17 must not overlap in time in order to operate ultrasound transducer 14 as a transmitter as well as a receiver. By varying parameter $t_3 - t_0$, i.e. the delay between the pulses generated by the two pulse generators, it is possible to select signals which were reflected in a certain distance to the ultrasound transducer, i.e. to "focus" on the fetal heart. For this purpose, pulse generator 17 may receive (on line 19) a control signal from a unit (such as a microprocessor) controlling the delay between the two pulses. It is understood that the width of the pulse generated by pulse generator 17, $t_4 - t_3$, is not necessarily the same as the pulse width of the pulses generated by pulse generator 7.

The pulse generated by pulse generator 17 are fed (via line 18) to a further mixer circuit 20 which also receives the high-frequency signal from HF generator 6. Mixer 10 generates a signal as depicted in FIG. 4e, i.e. high-frequency bursts which are delayed with respect to the transmitter pulses shown in FIG. 4d. The output of mixer 20 is fed (via line 21) to synchronous demodulator 16.

FIG. 4f depicts an example of the demodulated signal in prior art devices. Mixing of the signals results in bursts the envelope of which contains the Doppler frequency, i.e. demodulation has the effect of copying the Doppler shift (which was originally a shift of the 1 Mhz high frequency) into the low frequency band. The signal obtained by prior art demodulation as shown in FIG. 4f has then to be filtered. Furthermore, the signal is attenuated significantly (by a approximately $-42$ dB). Note that FIG. 4f is not drawn in the same scale as the other timing diagrams of FIG. 4.

It has to pointed out that the signal shown in FIG. 4f does NOT occur in the circuit according to FIG. 2. The details of demodulator 16 will be explained by the detailed diagram of FIG. 3, and its timing will be explained by means of FIGS. 5 and 6.

The output signal generated by demodulator circuit 16 is fed (via line 22) to a band pass 23. Its output 24 contains a low frequency signal with the frequency of the Doppler shift and may be further processed (not shown) in a frequency detector.

Figure 3:
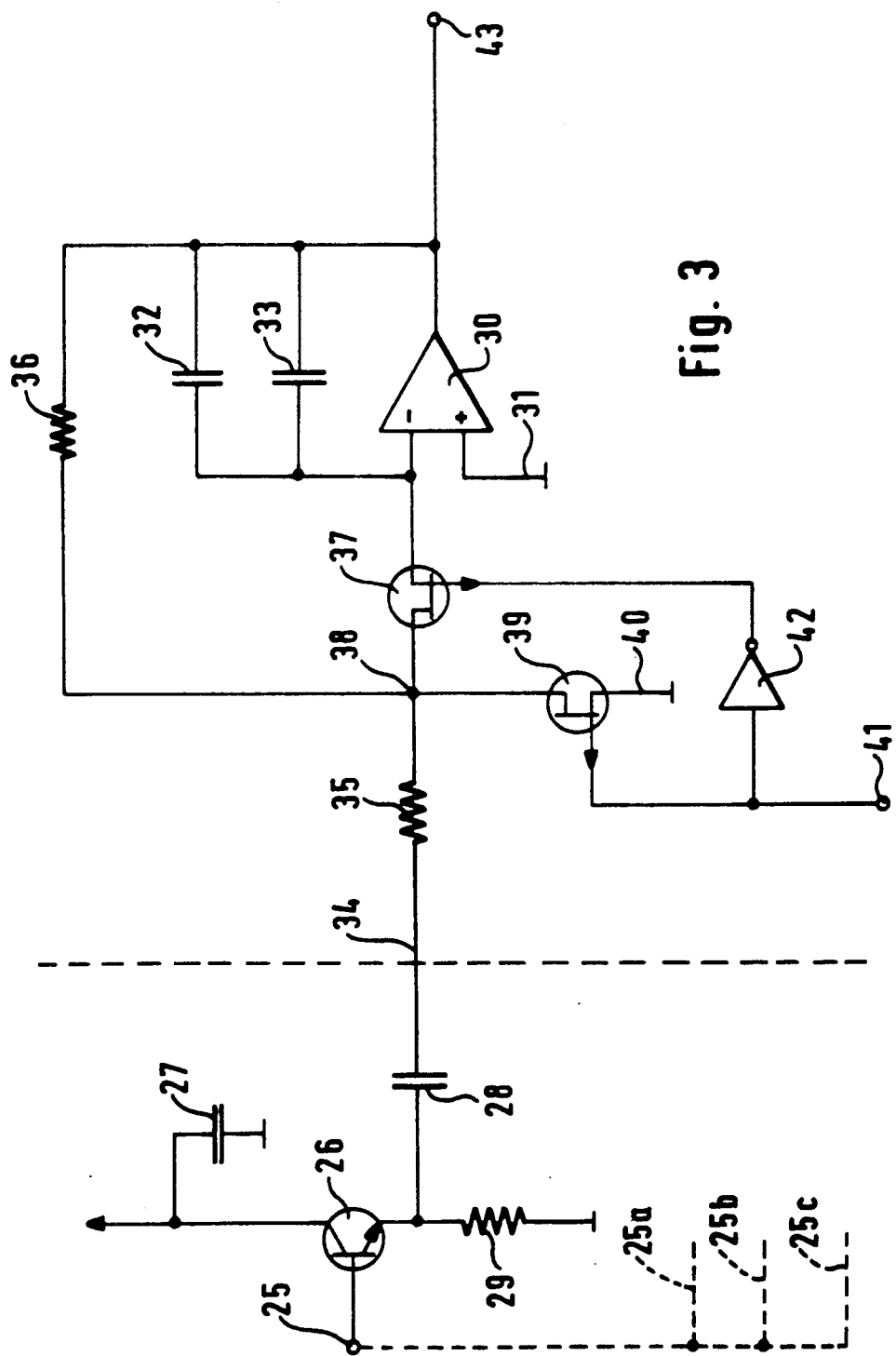
FIG. 3 is detailed diagram of the synchronous demodulator as part of the receiving section of the ultrasound channel.

The details of the demodulator circuit are shown in FIG. 3. A received ultrasound signal is converted into an electrical signal by the piezoelectric crystal of the ultrasound transducer and fed to input 25. The circuit consisting of transistor 26, capacitors 27 and 28 and resistor 29 operates as buffer amplifier and is not relevant for the demodulation of signal. Further signal paths may be connected in parallel to input 25, as indicated by dashed lines 25a to 25c.

The demodulator circuit comprises an operational amplifier 30 operated as inverting amplifier. Its non-inverting input is grounded (reference no. 31). Two feed-back capacitors 32 and 33 connect the output of operational amplifier 30 with its inverting input. Capacitor 32 has a capacitance of 2200 pF, and capacitor 33 has a capacitance of 3300 pF thus resulting in a total capacitance of 5500 pF. The parallel circuit of capacitors 32 and 33 is used to obtain a certain desired capacitance; it is understood that also only one capacitor may be used instead.

The output signal of the buffer amplifier is fed via line 34 to a resistor 35. This resistor operates, together with a second resistor 36, as a feedback loop determining the amplification of the system. Further, resistor 36 and capacitors 32 and 33 determine the time constant of the integrating circuit.

A field effect transistor (FET) of the self-conducting type (for example, a MOSFET of the depletion type) 37 connects node 38 (between resistors 35 and 36) with the inverting input of operational amplifier 30. Its drain is connected with node 38 and its source with the inverting input of operational amplifier 30. A further FET 39, also of the self-conducting type, connects node 38 with ground, the drain of FET 39 being connected with node 38 and its source with ground (reference no. 40).

A high-frequency signal (1 MHz) is fed to input 41. This is the signal generated by mixer 20 (FIG. 2) on line 21, depicted as a timing diagram in FIG. 4e. This signal is fed to the gate of FET 39. It is further fed to an inverter 42, and the inverted signal is fed to the gate of FET 37.

The output of operational amplifier 30 is labeled as 43.

The synchronous demodulator circuit operates as a signal demodulator as well as a low-pass filter and as a hold circuit thus drastically reducing component count. When the signal applied to input 41 is high (e.g. 5 Volts), FET 39 is in a high-impedance state which corresponds to an open switch. On the other hand, FET 37 is in the conducting state thus connecting node 38 with the inverting input of operational amplifier 30. In this mode, the circuit operates as a low-pass. Its time constant is determined by resistor 36 and the capacitance of capacitors 32 and 33. In the shown example, resistor 36 has a resistance of 1.21 kOhm, whereas the parallel circuit of capacitors 32 and 33 has a capacitance of 5500 pF. This results in a time constant of 6.65 $\mu$ which corresponds to a cutoff frequency of 23.9 kHz. This frequency is considerably lower than the 1 MHz frequency, and therefore the generated signal approximates the input signal only gradually. Further, the 1 MHz high frequency component is completely suppressed.

Resistor 36 determines, in connection with resistor 35, the amplification of the circuit. In the shown example, resistor 35 has a resistance of 1 kOhm thus resulting in an amplification of $V = -1.21$. If we additionally regard the ON resistance of FET 37 (approximately 200 Ohms), the amplification becomes $V = -1$.

The given values for resistors 35 and 36 and for capacitors 32 and 33 are adapted to register the fetal heart rate with a Doppler signal in the frequency range of 100 Hz to 480 Hz. Still it is also possible to adapt the circuit for fetal movement detection (5 Hz to 150 Hz). In this case, the following values are preferred for the passive components;
Resistor 35: 8.25 kOhms
Resistor 36: 17.8 kOhms
Capacitor 32: 3300 pF
Capacitor 33 is omitted.

This results in an amplification of $V = -2.1$ (if the ON resistance of FET 37 is also taken into account) and a time constant of 58.74 $\mu$s which corresponds to a cutoff frequency of 2.7 kHz.

When the signal at input 41 is low, FET 39 becomes conductive, i.e. connects node 38 with ground. At the same time, FET 37 enters the high-impedance state and interrupts the connection between node 38 and the inverting input of operational amplifier 30. In this mode, capacitors 32 and 33 are neither charged nor discharged and therefore hold their charge. The circuit then operates as a hold circuit. Grounding of node 38 has the effect that the input is loaded with a relatively constant current which is particularly important to avoid crosstalk on signal paths 25 to 25c. Further, no charges may pass FET 37 over its parasitic capacitance. FET 37 cannot enter the conductive state despite of its high gate potential.

Figure 5:
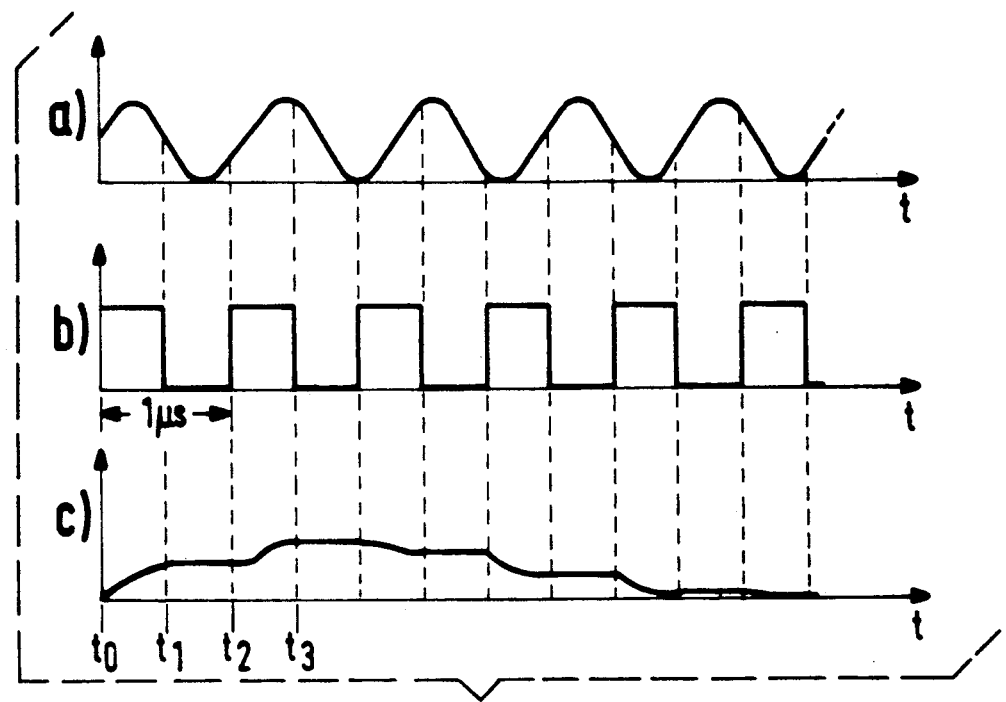
FIGS. 5a to 5c are timing diagrams to explain the operation of the demodulator circuit in the high-frequency range.
Figure 6:
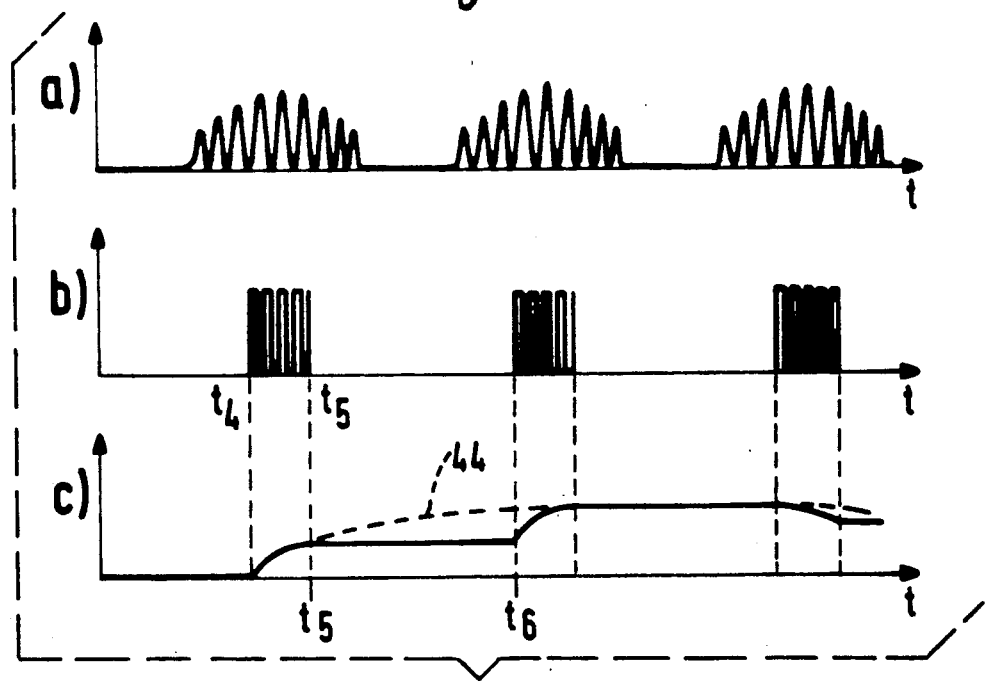
FIGS. 6a to 6c are timing diagrams to explain the operation of the demodulator circuit in other frequency bands.

Operation of the circuit shown in FIG. 3 will now be explained with reference to the timing diagrams in FIGS. 5 and 6. FIGS. 5a to 5c depict timing diagrams with a high resolution on the time axes, whereas FIGS. 6a to 6c have a low resolution on the time axes.

FIG. 5a depicts the incoming high-frequency ultrasound signal which was reflected by the walls of the fetal heart. This signal is present at line 34 and contains a Doppler shift in frequency.

The signal shown in FIG. 5b is the 1 MHz signal present at input terminal 41, also called "demodulator clock". When this signal is high ($t_0 < t < t_1$), the circuit operates as an integrator. The cutoff frequency of this integrator is considerably smaller than 1 MHz, i.e. its time constant is considerably longer than 1 $\mu$s. Therefore, the output (terminal 43) does not follow the input signal immediately, but rather approaches it slowly as depicted in FIG. 5c which depicts the output at terminal 43.

In the next 500 ns ($t_1 < t < t_2$), FET 39 becomes conductive which results in a potential of 0 Volts at node 38. At the same time, FET 37 enters the high-impedance state. Therefore, capacitors 32 and 33 are isolated each at one pin and therefore hold their charge. In this mode, the circuit operates as a hold circuit.

In the next period ($t_2 < t < t_3$), the circuit operates again as a low-pass filter, and so on.

FIG. 5c depicts the various operations which are performed by the demodulator circuit according to the invention. First, the high-frequency component (1 MHz) is removed. Due to the hold function, the signal is not attenuated. At the same time, demodulation is performed in that a heterodyne frequency equal to the frequency difference between the signals shown FIGS. 5a and 5b is generated. This frequency corresponds to the Doppler frequency shift of the ultrasound signal caused by the moving walls of the fetal heart. The signal shown in FIG. 5c contains the low-frequency component.

The Doppler component usually has a frequency in the range between 100 Hz and 480 Hz. For demonstration purposes, this Doppler frequency is overdrawn in FIGS. 5a to 5c. In reality, the frequency shift between the signals shown in FIG. 5a and 5b is smaller than drawn.

FIGS. 6a to 6c depict operation of the demodulator circuit upon a larger scale of the time axis. FIG. 6a depicts the received ultrasound signal present at line 34. This signal consists of thrusts which were reflected by moving tissue. The signals contain a Doppler shift with reference to the transmitter frequency of 1 MHz. As the walls of the fetal heart are not the only moving tissue, other tissue may also generate Doppler shifted components.

In order to filter out the signals reflected by the walls of the fetal heart, the demodulator clock depicted in FIG. 6b contains only oscillations during predefined "time windows", e.g. from time $t = t_4$ to $t = t_5$. The length of this time window and its phase shift with regard to the transmitted bursts may be adjustable, for example in dependance on the distance between the ultrasound transducer and the fetal heart.

As depicted in FIG. 6c, the time window of one receiving period (e.g., from $t = t_4$ to $t = t_3$) covers only a small part of an oscillation of the low-frequency Doppler signal. In the intervals between two receiving periods (e.g., from $t = t_5$ to $t = t_6$), the output of the circuit is held constant. This avoids considerable attenuation of the processed low-frequency signal.

As can be readily seen in FIG. 6c, the generated signal only contains the Doppler component as main frequency and some harmonics. These harmonics may be filtered out by an appropriate filter (indicated by block 23 in FIG. 2) for the generation of an ideal sinusoidal signal with the frequency of the Doppler shift. This ideal sinusoidal wave is indicated by the dashed line (reference no. 44) in FIG. 6c.

FIGS. 5c and 6c also depict that the demodulator circuit according to the present invention operates as a filter removing the high-frequency components.

The isolated Doppler component (output 43) is further fed to a frequency detector to indicate (display, record) the fetal heart rate. This method is well-known in the art, and therefore not illustrated in the drawings.

I claim:

1. An ultrasonic system, comprising:
   ultrasound transmitting means for emitting bursts of high-frequency ultrasound waves,
   ultrasound receiving means for receiving ultrasound waves reflected by said moving object, said ultrasound receiving means including a demodulator circuit which isolates a signal indicative of a Doppler component of the reflected ultrasound waves in order to determine the speed of said moving object in relation to said ultrasound transmitting means, said demodulator circuit comprising:
   an integrating circuit having a time constant which is considerably longer than the duration of a single oscillation of said reflected high frequency ultrasound waves;
   an actuatable switch coupled to an input of said integrating circuit;
   means for actuating said actuable switch with said reflected high frequency ultrasound waves at least during reception periods, and
   means for holding an output value of said integrating circuit during time intervals when said actuable switch is open.

2. The synchronous demodulator according to claim 1 wherein said integrating circuit comprises an operational amplifier.

3. The synchronous demodulator according to claim 2, wherein said integrating circuit comprises a feedback capacitor used in a first mode as the integrating element of a low-pass filter and used in a second mode as a holding element.

4. The synchronous demodulator according to claim 1, further comprising a second actuatable switch arranged between the input of said actuatable switch and a reference potential, said second actuatable switch being actuated in phase opposition to said first actuatable switch.

5. The synchronous demodulator according to claim 4 wherein at least one of said switches comprises a field effect transistor.

6. A method for demodulating an ultrasound signal consisting of high-frequency burst waves reflected by a moving object, comprising the steps of:
   feeding the ultrasound signal to a circuit;
   applying an actuating signal to said circuit; and
   alternatively switching said circuit between a low-pass filter mode and a storage circuit mode in response to said actuating signal.

7. The method according to claim 6, wherein said actuating signal is only applied to said circuit during reception periods for the selection of moving objects within a certain distance.

8. The method according to claim 6 wherein said actuating signal actuates a first switch in an input line of a low-pass filter/storage circuit.

9. The method according to claim 8 wherein the inverse of said actuating signal actuates a second switch connecting the input of said first switch with a reference potential.

10. A demodulator circuit for demodulating ultrasound burst waves reflected by a moving object, comprising:
    an integrating circuit having a time constant which is considerably longer than the duration of a single oscillation of said reflected ultrasound burst waves;
    an actuatable switch coupled to an input of said integrating circuit;
    means for actuating said actuatable switch with said reflected ultrasound burst waves at least during reception periods; and
    means for holding an output value of said integrating circuit during time intervals when said actuatable switch is open.

* * * * *

UNITED STATES PATENT AND TRADEMARK OFFICE
CERTIFICATE OF CORRECTION

PATENT NO. : 5,097,837
DATED : March 24, 1992
INVENTOR(S) : Joerg Reuschel

It is certified that error appears in the above-identified patent and that said Letters Patent is hereby corrected as shown below:

Column 1, line 20, change "ma" to --may--.

Column 5, line 31, after "µs" delete --and more--.

Column 9, line 30, change "actuable" to --actuatable--.

Signed and Sealed this

Thirty-first Day of August, 1993

*Attest:*

BRUCE LEHMAN

*Attesting Officer*    *Commissioner of Patents and Trademarks*